US008828666B2

(12) United States Patent
Sakita et al.

(10) Patent No.: US 8,828,666 B2
(45) Date of Patent: Sep. 9, 2014

(54) METHOD FOR MEASURING BONDING ACTIVITY OF ANTIBODY WHICH MIMICS ANTIBODY-DEPENDENT CELL MEDICATED CYTOTOXIC ACTIVITY

(75) Inventors: Masashi Sakita, Tokyo (JP); Takayuki Yoshimori, Tokyo (JP)

(73) Assignee: Chugai Seiyaku Kabushiki Kaisha, Tokyo (JP)

( * ) Notice: Subject to any disclaimer, the term of this patent is extended or adjusted under 35 U.S.C. 154(b) by 842 days.

(21) Appl. No.: 12/452,147

(22) PCT Filed: Jun. 17, 2008

(86) PCT No.: PCT/JP2008/061049
§ 371 (c)(1),
(2), (4) Date: Mar. 22, 2010

(87) PCT Pub. No.: WO2008/156083
PCT Pub. Date: Dec. 24, 2008

(65) Prior Publication Data
US 2010/0190266 A1    Jul. 29, 2010

(30) Foreign Application Priority Data
Jun. 18, 2007    (JP) ................... 2007-160007

(51) Int. Cl.
*G01N 33/53*    (2006.01)
(52) U.S. Cl.
CPC ..................................... *G01N 33/53* (2013.01)
USPC ........... 435/7.1; 435/7.92; 436/164; 436/172; 436/501

(58) Field of Classification Search
None
See application file for complete search history.

(56) References Cited

U.S. PATENT DOCUMENTS

| 5,998,146 A * | 12/1999 | Latva et al. ................... 435/6.11 |
| 7,741,128 B2 * | 6/2010 | Su ................................. 436/501 |
| 2003/0166146 A1 * | 9/2003 | Lee et al. ...................... 435/69.1 |
| 2010/0092997 A1 * | 4/2010 | Nakamura et al. ............. 435/7.1 |

FOREIGN PATENT DOCUMENTS

| JP | 10-319017 A | 12/1998 |
| WO | WO 00/43780 A1 | 7/2000 |
| WO | WO 2006/101520 A2 | 9/2006 |
| WO | WO 2006/114700 A3 | 11/2006 |

OTHER PUBLICATIONS

Blomberg et al., Terbium and Rhodamine as Labels in a Homogeneous Time-resolved Flurometric Energy Transfer Assay, Clinical Chemistry 45:6, 1999, pp. 855-861.*
International Preliminary Report on Patentability and Written Opinion mailed Jan. 7, 2010, in PCT/JP2008/061049, 6 pages, Jan. 7, 2010.
Supplementary European Search Report dated Jul. 8, 2010, in corresponding EP 08777287.7, 12 pages, Jul. 8, 2010.
Office Action issued Apr. 6, 2011, in corresponding EP 08777287.7, 8 pages, Apr. 6, 2011.
Mishima, Yuji, "Kotai Iyaku up to date—Gan Hen Kotai Iyaku no Hotai Izonsei, Kotai Izonsai Satsusaibo Koka," Pharma. Med., Mar. 10, 2007, 25(3):9-13.
Ozaki et al., "M Tampakukessho no Kiso to Rinsho 8 Kotsuzuishu ni Taisuru Shinki no Kotai Ryoho Tokuni Ko HM1.24 Kotai Ryoho ni Tsuite," Ketsueki Frontier, May 2002, 12(5):651-659.
Sumiya, Morito, "ADCC no Sokutei Hoho," Clinical Testing, May 1984, 28(5):564-569.
Suzuki, Tatsuo, "ADCC Kensa," The Japanese Journal of Clinical Pathology, Apr. 1981, 45:273-282.
Yano, Keisuke, "ADCC no Kijo," Clinical Immunology, Feb. 1981, 13(2):116-124.

* cited by examiner

*Primary Examiner* — Gary W Counts
(74) *Attorney, Agent, or Firm* — Foley & Lardner LLP

(57) ABSTRACT

The present invention provides a simple method which is capable of evaluating the binding activities of an antibody to both an antigen and an Fc receptor. Disclosed is a method of measuring the binding activities of an antibody to both an antigen or antigen epitope and an Fc receptor or a fragment thereof, comprising a step of mixing the antibody with the antigen or antigen epitope labeled with one member of a set of donor and acceptor capable of fluorescent resonance energy transfer and the Fc receptor or fragment thereof labeled with the other member of the set of donor and acceptor; a step of irradiating the resultant mixture with light having a wavelength capable of exciting the donor; and a step of measuring the fluorescence level of the mixture. Also provided are a method of estimating the ADCC activity of an antibody, a method of controlling the quality of an antibody, a method of manufacturing an antibody, a method of screening for antibodies, and kits for use in these methods.

3 Claims, 5 Drawing Sheets

Std is Lot No. ON0305J01 (aFuc 4.5%).

SEQUENCE LISTING

```
<160> NUMBER OF SEQ ID NOS: 6

<210> SEQ ID NO 1
<211> LENGTH: 20
<212> TYPE: PRT
<213> ORGANISM: Homo sapiens

<400> SEQUENCE: 1

Ser Gln Gln Ala Thr Pro Lys Asp Asn Glu Ile Ser Thr Phe Asn His
1               5                   10                  15

Leu Gly Asn Val
            20

<210> SEQ ID NO 2
<211> LENGTH: 181
```

<212> TYPE: PRT
<213> ORGANISM: Homo sapiens

<400> SEQUENCE: 2

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
                20                  25                  30

Tyr Ser Pro Glu Asp Asn Ser Thr Gln Trp Phe His Asn Glu Ser Leu
            35                  40                  45

Ile Ser Ser Gln Ala Ser Ser Tyr Phe Ile Asp Ala Ala Thr Val Asp
        50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
130                 135                 140

Thr Leu Lys Asp Ser Gly Ser Tyr Phe Cys Arg Gly Leu Val Gly Ser
145                 150                 155                 160

Lys Asn Val Ser Ser Glu Thr Val Asn Ile Thr Ile Thr Gln Gly His
                165                 170                 175

His His His His His
            180

<210> SEQ ID NO 3
<211> LENGTH: 181
<212> TYPE: PRT
<213> ORGANISM: Homo sapiens

<400> SEQUENCE: 3

Arg Thr Glu Asp Leu Pro Lys Ala Val Val Phe Leu Glu Pro Gln Trp
1               5                   10                  15

Tyr Arg Val Leu Glu Lys Asp Ser Val Thr Leu Lys Cys Gln Gly Ala
                20                  25                  30

Tyr Ser Pro Glu Asp Asn Ser Thr Gln Trp Phe His Asn Glu Ser Leu
            35                  40                  45

Ile Ser Ser Gln Ala Ser Ser Tyr Phe Ile Asp Ala Ala Thr Val Asp
        50                  55                  60

Asp Ser Gly Glu Tyr Arg Cys Gln Thr Asn Leu Ser Thr Leu Ser Asp
65                  70                  75                  80

Pro Val Gln Leu Glu Val His Ile Gly Trp Leu Leu Leu Gln Ala Pro
                85                  90                  95

Arg Trp Val Phe Lys Glu Glu Asp Pro Ile His Leu Arg Cys His Ser
            100                 105                 110

Trp Lys Asn Thr Ala Leu His Lys Val Thr Tyr Leu Gln Asn Gly Lys
        115                 120                 125

Gly Arg Lys Tyr Phe His His Asn Ser Asp Phe Tyr Ile Pro Lys Ala
130                 135                 140

Thr Leu Lys Asp Ser Gly Ser Tyr Phe Cys Arg Gly Leu Phe Gly Ser
145                 150                 155                 160

```
Lys Asn Val Ser Ser Glu Thr Val Asn Ile Thr Ile Thr Gln Gly His
            165                 170                 175
His His His His His
            180

<210> SEQ ID NO 4
<211> LENGTH: 14
<212> TYPE: PRT
<213> ORGANISM: Homo sapiens

<400> SEQUENCE: 4

Asp Val Ser Thr Ala Val Ser Phe Tyr Ser Tyr Thr Thr Pro
1               5                   10

<210> SEQ ID NO 5
<211> LENGTH: 34
<212> TYPE: DNA
<213> ORGANISM: Artificial
<220> FEATURE:
<223> OTHER INFORMATION: Primer

<400> SEQUENCE: 5
taagaattcc caccatgtgg cagctgctcc tccc                          34

<210> SEQ ID NO 6
<211> LENGTH: 57
<212> TYPE: DNA
<213> ORGANISM: Artificial
<220> FEATURE:
<223> OTHER INFORMATION: Primer

<400> SEQUENCE: 6
taagcggccg cttatcaatg atgatgatga tgatgacctt gagtgatggt gatgttc   57
```

METHOD FOR MEASURING BONDING ACTIVITY OF ANTIBODY WHICH MIMICS ANTIBODY-DEPENDENT CELL MEDICATED CYTOTOXIC ACTIVITY

CROSS-REFERENCE TO RELATED APPLICATIONS

This application is a National Stage application of PCT/JP2008/061049, filed Jun. 17, 2008, which claims priority from Japanese application JP 2007-160007, filed Jun. 18, 2007.

TECHNICAL FIELD

The present invention relates to a method of measuring the binding activities of an antibody to both an antigen and an Fc receptor. More specifically, the present invention relates to a method of measuring the binding activities of an antibody to both an antigen and an Fc receptor using time-resolved fluorescent resonance energy transfer.

BACKGROUND ART

The human body is equipped with a defense system called immunity. When a foreign substance such as bacterium or virus (antigen) enters the body, a protein called antibody is produced and attacks the antigen to protect the living body. Antibody medicine is a medicine using this effect of antibody. As the mechanisms of action of antibody medicine, activities such as antibody-dependent cell-mediated cytotoxicity (ADCC), complement-dependent cytotoxicity (CDC), neutralizing activity or apoptosis induction activity have been reported to be important. In particular, it has been reported that Fc receptor-mediated ADCC activity is the most important antitumor mechanism in Herceptin (therapeutic for metastatic breast cancer) and Rituxan (therapeutic for non-Hodgkin's lymphoma) (Non-Patent Document 1).

The effect of ADCC injures a target cell through the binding of an antibody to an antigen expressed on the target cell and the binding of the Fc portion of the antibody to an Fc receptor expressed on an effecter cell. Two binding activities, i.e., antigen-antibody binding activity and Fc/Fc receptor binding activity, are believed to be necessary for the manifestation of the effect of ADCC. Although antigen-antibody binding activity can be conventionally evaluated by competitive ELISA (cELISA) (Non-Patent Document 2) (FIG. 1), no method has been known to measure Fc/Fc receptor binding activity, to say nothing of a method to evaluate the above-mentioned two binding activities simultaneously.

Non-Patent Document 1: Clybes, R. A., et al., 2000. Inhibitory Fc receptors modulate in vivo cytoxicity against tumor targets. Natl. Med. 6: 443

Non-Patent Document 2: Human monoclonal antibody stability and activity at vaginal pH, Journal of Reproductive Immunology 56, 61-76 (2001)

DISCLOSURE OF THE INVENTION

Problem for Solution by the Invention

It is an object of the present invention to provide a simple method which is capable of evaluating the binding activities of an antibody to both an antigen and an Fc receptor.

Means to Solve the Problem

In view of the mode of action of ADCC in which the effect is produced upon the binding of an antibody to both an antigen and an Fc receptor, the present inventors considered that a test system that can evaluate antigen-antibody binding activity and Fc/Fc receptor binding activity simultaneously would be optimal, compared to a system that evaluates these two activities separately. Then, using the principle of time-resolved, fluorescent resonance energy transfer (TR-FRET), the present inventors have established a novel evaluation method in which fluorescence can be detected only when the binding of an antibody to an antigen and its binding to an Fc receptor occur simultaneously. This evaluation method is applicable to evaluation of the CDC activity of antibodies or evaluation of the binding activity of bi-specific antibodies.

The present invention may be summarized as follows.

(1) A method of measuring the binding activities of an antibody to both an antigen or antigen epitope and an Fc receptor or a fragment thereof, comprising:
    a step of mixing the antibody with the antigen or antigen epitope labeled with one member of a set of donor and acceptor capable of fluorescent resonance energy transfer and the Fc receptor or fragment thereof labeled with the other member of the set of donor and acceptor;
    a step of irradiating the resultant mixture with light having a wavelength capable of exciting the donor; and
    a step of measuring the fluorescence level of the mixture.

(2) A method of estimating the antibody-dependent cell-mediated cytotoxicity of an antibody based on its binding activities measured by the method of (1).

(3) A method of controlling the quality of an antibody, using the method of (1) or (2).

(4) A method of manufacturing an antibody, comprising a step of controlling the quality of the antibody by the method of (3).

(5) A method of manufacturing a medicament comprising an antibody manufactured by the method of (4).

(6) A method of screening for antibodies having a desired binding activity or antibody-dependent cell-mediated cytotoxicity, using the method of (1) or (2).

(7) A kit for use in the method of any one of (1) to (3) or (6), comprising the following (a) to (c):
    (a) a set of donor and acceptor capable of fluorescent resonance energy transfer
    (b) an antigen or antigen epitope
    (c) an Fc receptor or a fragment thereof (8) A method of measuring the binding activities of an antibody to both an antigen or antigen epitope and an antibody-binding molecule or a fragment thereof, comprising:
    a step of mixing the antibody with the antigen or antigen epitope labeled with one member of a set of donor and acceptor capable of fluorescent resonance energy transfer and the antigen-binding molecule or fragment thereof labeled with the other member of the set of donor and acceptor;
    a step of irradiating the resultant mixture with light having a wavelength capable of exciting the donor; and
    a step of measuring the fluorescence level of the mixture.

(9) The method of (8), wherein the antibody-binding molecule is selected from the group consisting of an Fc receptor, a complement molecule and an antigen or antigen epitope, provided that the antigen or antigen epitope is different from the antigen or antigen epitope labeled with one member of the set of donor and acceptor capable of fluorescent resonance energy transfer.

(10) A method of screening for antibodies with a biological activity that results from binding to both a desired antigen or antigen epitope and a desired antibody-binding molecule or a fragment thereof, using the method of (8) or (9).

(11) A kit for use in the method of any one of (8) to (11), comprising the following (a) to (d):
(a) a set of donor and acceptor capable of fluorescence resonance energy transfer
(b) an antigen or antigen epitope
(d) an antibody-binding molecule or a fragment thereof.

Effect of the Invention

According to the present invention, it has become possible to evaluate the binding activities of an antibody according to the mode of action of ADCC.

The present specification encompasses the contents described in the specification and/or drawings of Japanese Patent Application No. 2007-160007 based on which the present patent application claims priority.

BEST MODE FOR CARRYING OUT THE INVENTION

Figure 1:
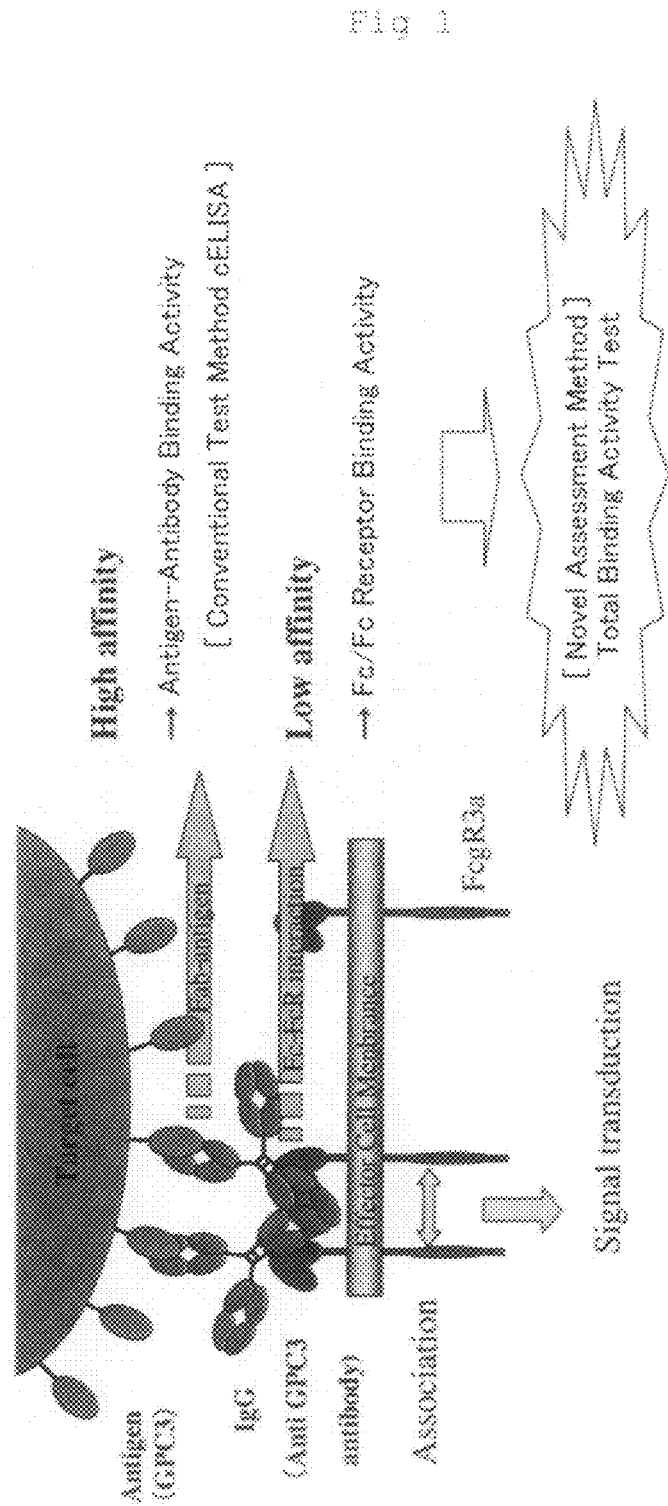
FIG. 1 is a schematic drawing showing the mode of action of ADCC of antibodies.

Hereinbelow, the embodiments of the present invention will be described in more detail.

The method of the present invention uses fluorescent resonance energy transfer (FRET), a phenomenon that occurs when a donor and an acceptor are in sufficient proximity. Briefly, when the donor is excited, the excitation energy is transferred to the acceptor located in proximity by means of resonance energy transfer. As a result, fluorescence with a longer wavelength than the excitation light can be observed. When a fluorescent lanthanide chelate that shows an excited state of a long life (of millisecond order) is used as a donor, several hundred microseconds are required for energy transfer to an acceptor. Therefore, by measuring the fluorescence intensity by a time-resolved measuring method (TR) after an appropriate delay time, it is possible to inhibit background fluorescence (e.g., fluorescence caused by non-specific proximity of the donor and acceptor). Furthermore, since lanthanide chelates have a very wide Stokes shift (e.g., in the case of europium chelate, excitation wavelength is 340 nm and fluorescence wavelength is 615 nm), such chelates have an advantage that background influence can be suppressed to a minimum level.

Conventionally, binding activity between antigen and antibody has been performed by ELISA. Further, it was reported that conformational changes in the constant region of an antibody resulting from the binding of the antibody to an antigen were detected by BIACORE (International Immunology, Vol. 15, No. 3, pp. 417-426 (2003)). However, this report was short of confirming that antibody affinity for Fc receptor increased as a result of the conformational changes. As shown in Examples described later, the present inventors observed that a mixture of an acceptor-labeled antigen, a donor-labeled Fc receptor and an antibody caused FRET. This demonstrates the conformational changes of the antibody according to the mode of action of ADCC, as well as the generation of a new mode of binding. Therefore, it can be said that the present inventors have established a method of measuring the binding activity of an antibody which is believed to correspond to its ADCC activity.

Further, in the measurement of CDC activity which is activated by the binding of a complement (C1) to a specific site of an antibody bound to an antigen's molecule, it becomes possible to measure CDC activity as well as ADCC activity by labeling the antigen and the complement (e.g., C1 such as C1q, C1r or C1s or C2, C3 or C4, preferably C1) with an acceptor or a donor.

Still further, when the antibody is a bi-specific antibody, the measuring method of the present invention is also applicable to the measurement of the binding activities of the bi-specific antibody by labeling each antigens's molecule with an acceptor or a donor.

Thus, the method of the present invention is an excellent method for measuring the biological activity generated specifically when an antibody binds to an antigen as well as to other antigen-binding molecule simultaneously (e.g., ADCC activity, CDC activity, the binding activity of bi-specific antibodies, etc.).

The present invention provides a method of measuring the binding activities of an antibody to both an antigen or antigen epitope and an Fc receptor or a fragment thereof (hereinafter referred to as "total binding activity"), comprising a step of mixing the antibody with the antigen or antigen epitope labeled with one member of a set of donor and acceptor capable of fluorescent resonance energy transfer and the Fc receptor or fragment thereof labeled with the other member of said set of donor and acceptor; a step of irradiating the resultant mixture with light having a wavelength capable of exciting the donor; and a step of measuring the fluorescence level of the mixture. The measurement of the fluorescence level of the mixture may be performed after the background fluorescence has been quenched.

Further, the present invention provides a method of measuring the binding activities of an antibody to both an antigen or antigen epitope and an antibody-binding molecule or a fragment thereof, comprising a step of mixing the antibody with the antigen or antigen epitope labeled with one member of a set of donor and acceptor capable of fluorescence resonance energy transfer and the antigen-binding molecule or fragment thereof labeled with the other member of said set of donor and acceptor; a step of irradiating the resultant mixture with light having a wavelength capable of exciting the donor; and a step of measuring the fluorescence level of the mixture. Examples of the antibody-binding molecule include Fc receptors, complement molecules, antigens or antigen epitopes (these antigens or antigen epitopes are different from the antigen or antigen epitope labeled with one member of the set of donor and acceptor capable of fluorescent resonance energy transfer).

As an antibody whose total binding activity can be measured by the method of the present invention, any antibody may be used as long as it has both antigen binding activity and Fc receptor binding activity when ADCC activity is to be measured. When CDC activity is to be measured, any antibody may be used as long as it has both antigen binding activity and complement (C1) binding activity. When the binding activity of a bi-specific antibody is to be measured, any antibody may be used as long as it has two different antigen binding domains.

When the antibody used in the method of the present invention is a whole antibody, the antibody class thereof is not particularly limited. An antibody of any class (such as IgG; IgM, IgE or IgA) may be used; preferably, an antibody of IgG or IgM class is used. This antibody may be any one of a monoclonal antibody, a chimeric antibody or a humanized antibody. Also included in the antibodies which may be used in the method of the present invention are degraded antibodies with an antigen binding domain and an Fc receptor binding domain, degraded antibodies with an antigen binding domain and a complement (C1) binding domain, and bi-specific degraded antibodies.

Examples of donors capable of fluorescent resonance energy transfer include, but are not limited to, lanthanide chelates in which a ligand 2,2',2",2'''-[(4'-4-aminophenyl)-2, 2':6',2"-terpypyridine-6,6"-diyl)bis(methylenenitrilo)]tetrakis (acetic acid) is coordination bonded to a lanthanide [europium (Eu), terbium (Tb), samarium (Sa) or dysprosium (Dy)]. Lanthanide chelates are preferable because they show an excited state of a long life (of millisecond order) and have a long Stokes shift.

Examples of acceptors capable of fluorescent resonance energy transfer include, but are not limited to, allophycocyanin, ULight, Alexa, HiLyte Fluor, HyCY-5, B-PE (B-phycoerythrin) and R-PE (R-phycoerythrin). All of these acceptors are capable of transferring the excitation energy of a lanthanide chelate such as europium chelate.

The antigen to be used in the method of the present invention is not particularly limited. Any antigen having an antigenic activity may be used. Specific examples include, but are not limited to, glypican-3, HER2, CD20, CD3, TNF, CD25, RSV, CD33, CD53, VEGF, IL6-R and TNF. Further, the antigen need not be of a full length but its epitope region may be used. For example, a region consisting of the amino acid sequence shown in SEQ ID NO: 1 may be used as the epitope region of glypican-3. As the epitope region of VEGF, DVSTAVSFYSYTTP (SEQ ID NO: 4) may be used (High-affinity human antibodies from Phage-displayed synthetic Fab libraries with a single framework scaffold, J. Mol. Biol. 340 pp. 1073-1093 (2004)).

Fc receptor (FcR) is a receptor for the Fc region of immunoglobulin (Ig) and expressed in most of macrophages, neutrophils, mast cells and immunocompetent cells. FcRs for immunoglobulins of IgG, IgE and IgA classes are called FcγR, FcεR and FcαR, respectively. FcγR is classified into three major groups of FcγRI, FcγRII and FcγRIII. It is believed that FcγRIII expressed on the surfaces of NK cells is a mediator of ADCC.

The fragment of Fc receptor may be any fragment as long as it retains the biological activity of Fc receptor. As a fragment of FcγRIII, a fragment consisting of the amino acid sequence shown in SEQ ID NO: 2 or SEQ ID NO: 3 may be used. Other fragments of Fc receptors are described, for example, in Betty D. Louis B. and Barbara K., "Site of Binding of IgG2b and IgG2a by Mouse Macropharge Fc receptors by using Cyanogen bromide fragments", The Journal of Immunology, Vol. 134 No. 2 (1985) pp. 1080-1083.

An antigen or antigen epitope and an Fc receptor or a fragment thereof are used after they are labeled, directly or indirectly, with a donor or an acceptor that are capable of fluorescent resonance energy transfer.

For example, anti-6XHis antibody labeled with europium chelate is commercially available. Therefore, if 6XHis is added to an appropriate site of an antigen (or antigen epitope) or an Fc receptor (or a fragment thereof), it is possible to label the antigen (or antigen epitope) or the Fc receptor (or a fragment thereof) with the donor by allowing the formation of a complex with the anti-6XHis antibody (antigen-antibody reaction). Also available commercially are europium chelate-labeled protein G, anti-human IgG antibody, anti-mouse IgG antibody, anti-rabbit IgG antibody, streptavidin, biotin, ubiquitin, anti-GST antibody, anti-DNP antibody, anti-c-Myc antibody, anti-FLAG antibody, anti-HA antibody, and the like. These products may be used in the present invention.

Streptavidin-linked allophycocyanin is also available commercially. Therefore, if biotin is attached to an appropriate site of an antigen (or antigen epitope) or an Fc receptor (or a fragment thereof), it is possible to label the antigen (or antigen epitope) or the Fc receptor (or a fragment thereof) with the acceptor by allowing the formation of a complex with avidin. Also available commercially are allophycocyanin-bound anti-c-Myc antibody, anti-FLAG antibody, anti-GST antibody, anti-mouse IgG antibody, anti-rabbit IgG antibody, wheat germ agglutinin, anti-DNP antibody, anti-6XHis antibody, anti-HA antibody, biotin, protein A, WGA, concanavalin A, and the like. These products may be used in the present invention.

Figure 2:
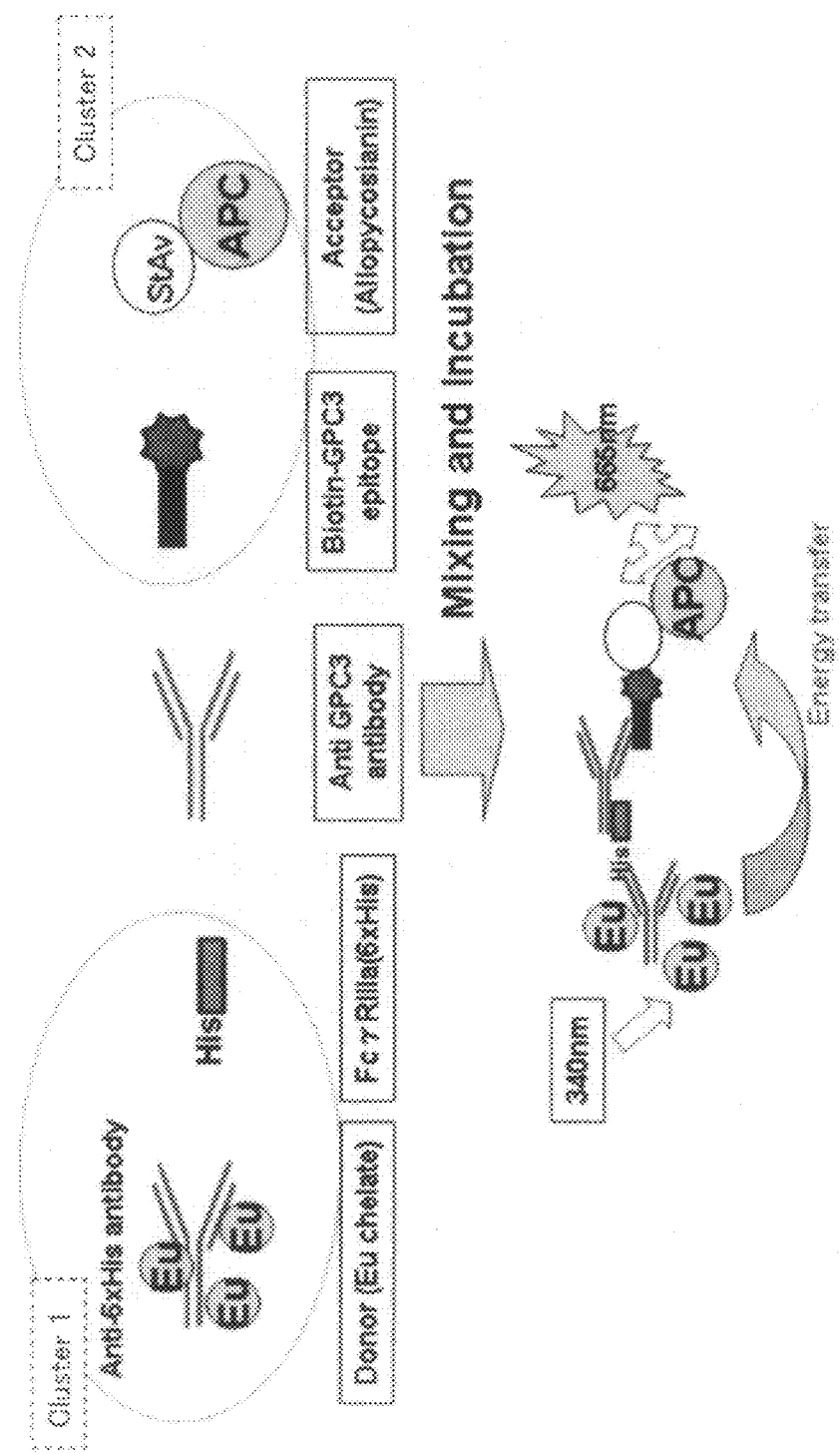
FIG. 2 is a schematic drawing showing the principle of the method of the present invention for measuring antibody binding activities (total binding activity).

An antigen (or antigen epitope) labeled as described above with one member of a set of donor and acceptor capable of fluorescent resonance energy transfer and an Fc receptor (or a fragment thereof) labeled with the other member of the set are mixed with an antibody and then incubated for an appropriate time period. The appropriate concentrations of donor and acceptor are selected such that the level of fluorescence emitted from the acceptor as a result of FRET between the donor and the acceptor is 100 counts or more, preferably 500 counts or more, and more preferably 1000 counts or more. The upper limit of the level of fluorescence emitted from the acceptor as a result of FRET between the donor and the acceptor is not particularly fixed. However, the appropriate upper limit is 2,500,000 counts, preferably 2,000,000 counts, and more preferably 1,800,000 counts. As a result, a complex of the antigen (or antigen epitope) and the antibody is first formed. This causes the conformation change of the antibody, increasing its affinity for the Fc receptor (or a fragment thereof). Consequently, it is believed that the distance between the donor and the acceptor present on the antigen or the Fc receptor becomes shorter. When this three-component complex is irradiated with excitation light, fluorescent resonance energy transfer occurs between the donor and the acceptor, and fluorescence with a wavelength longer than the excitation light is observed (FRET) (FIG. 2). By integrating the fluorescence level for a specific time period (TR) and by delaying the time of measurement, it becomes possible to detect a fluorescent signal with little background fluorescence caused by non-specific proximity of the donor and the acceptor.

The time period for incubating the mixture of an antigen (or antigen epitope), an Fc receptor (or a fragment thereof) and an antibody is not particularly limited. Usually, the mixture is incubated for 30-180 min, preferably 45-120 min.

When an antibody is to be mixed with an antigen (or antigen epitope) and an Fc receptor (or a fragment thereof), the antibody may be diluted with a buffer (e.g., buffer containing Tris-HCl, EDTA, NaCl, TRITON™ X-100 (Polyethylene glycol octylphenol ether), DTT, etc.) or the like.

The wavelength of the excitation light may be any wavelength as long as it is capable of exciting a donor. For example, when the donor is europium chelate, an optical filter of 320 nm may be used to apply the excitation light. The application of excitation light may be performed, for example, 300 times (of flashing) using an optical filter of 320 nm (bandwidth: 75 nm).

The detection of fluorescent signal may be performed under conditions where the background signal is inhibited. Such conditions may be appropriately selected depending on the target of measurement.

For example, when the donor is europium chelate and the acceptor is allophycocyanin, excitation light may be applied 300 times of flashing through an optical filter of 320 nm (bandwidth: 75 nm), and then the resultant signal may be measured after a delay time of 70 μs with optical filters of 665 nm (bandwidth: 7.5 nm) and 615 nm (bandwidth: 8.5 nm) for a window time (measuring time) of 400 μs.

The measuring condition of TR-FRET may be altered appropriately depending on the types of donor and acceptor used.

The measurement of fluorescence may be performed by determining the level of fluorescence emitted from the acceptor as a result of FRET between the donor and the acceptor. When the donor or the acceptor emits fluorescence by direct excitation, the level of the emitted fluorescence may also be measured. The fluorescence emitted by the donor or the acceptor as a result of direct excitation may be used as an internal standard. For example, when the donor is europium chelate and the acceptor is allophycocyanin, signal intensity may be corrected with the ratio (percentage, permillage, etc.) of the level of fluorescence emitted from the acceptor by FRET (fluorescence at wavelength of 665 nm) to the level of fluorescence emitted from the donor by direct excitation (fluorescence at wavelength of 615 nm), to thereby state the total binding activity. Since the method of the present invention for measuring antibody binding activity evaluates the binding mode of an antibody according to the mode of action of ADCC, it is believed that the antibody binding activity (total binding activity) measured by the method of the invention is highly correlated with ADCC activity. Thus, it is possible to estimate ADCC activity from the total binding activity. For example, if a calibration curve showing the correlation between total binding activity and ADCC activity is prepared in advance, ADCC activity may be estimated easily from the total binding activity measured. Similarly, in the case of measuring the CDC activity of an antibody or the binding activities of a bi-specific antibody, these biological activities can be easily estimated from the total binding activity measured by the present invention.

This total binding activity is applicable to quality control of antibodies, screening methods for optimization of antibodies, methods of evaluating the biological activities of antibodies, and so forth.

Quality control of antibodies may be performed as one step in the antibody manufacturing process. The present invention also encompasses a method of manufacturing an antibody, including a step of controlling antibody quality. The present invention also encompasses a method of manufacturing a medicament comprising an antibody manufactured by the above-described method.

Antibodies may be produced by administering an antigen or antigen epitope to an animal using a conventional protocol. The antibody to be used in the present invention may be either a polyclonal antibody, monoclonal antibody, chimeric antibody or humanized antibody.

Polyclonal antibodies may be produced according to a known method with or without necessary modifications. For example, an immunizing antigen is administered to an animal (for immunization); then, a material containing antibodies to the immunizing antigen is collected from the immunized animal; and the antibodies are isolated and purified. In the antigen administration, complete Freund's adjuvant or incomplete Freund's adjuvant may be administered for enhancing the antibody producing ability of the animal. Usually, antigen administration is performed once for every about 2 to 6 weeks to give a total of about 2 to 10 administrations.

Polyclonal antibodies may be collected from the blood, abdominal dropsy or the like (preferably blood) of the immunized animal. Isolation and purification of polyclonal antibodies may be performed according to methods of isolation/purification of immunoglobulin (e.g., salting out, alcohol precipitation, isoelectric precipitation, electrophoresis, adsorption/desorption with ion exchangers, ultra-centrifugation, gel filtration, or a specific purification method in which antibodies alone are collected with an antigen-bound solid phase or an active adsorbent such as protein A or protein G, followed by dissociation of the binding).

Monoclonal antibodies may be produced according to the hybridoma method of G. Koehler and C. Milstein described in Nature (1975) 256: 495 and Science (1980) 208: 692-. Briefly, after immunization of an animal, antibody producing cells are isolated from the spleen of the immunized anima and fused to myeloma cells to thereby prepare monoclonal antibody-producing cells. Further, those cell systems that specifically react with the antigen or antigen epitope used but which do not substantially cross-react with other antigenic proteins may be isolated. The cell systems are then cultured, and desired monoclonal antibodies may be obtained from the culture of these cell systems. Purification of monoclonal antibodies may be performed according to the above-listed methods of isolation/purification of immunoglobulin.

Techniques for preparing humanized antibodies are described in Biotechnology 10, 1121-, 1992; and Biotechnology 10, 169-, 1992.

The antibody manufactured by the method of the present invention may be mixed with pharmaceutically acceptable carriers or additives and the resultant mixture formulated to manufacture a medicament.

Examples of pharmaceutically acceptable carriers or additives include, but are not limited to, water, pharmaceutically acceptable organic solvents, collagen, polyvinyl alcohol, polyvinylpyrrolidone, carboxyvinyl polymers, carboxymethylcellulose sodium, sodium polyacrylate, sodium alginate, water-soluble dextran, carboxymethylstarch sodium, pectin, methylcellulose, ethylcellulose, xanthan gum, gum arabic, casein, agar, polyethylene glycol, diglycerin, glycerin, propylene glycol, vaseline, paraffin, stearyl alcohol, stearic acid, human serum albumin (HSA), mannitol, sorbitol, lactose, and surfactants acceptable as pharmaceutical additives.

In practice, additives are selected from the above-listed materials, either alone or in appropriate combinations, depending on the dosage form of medicament. Needless to say, additives are not limited to those listed above. For example, for use as an injection, a purified antibody may be dissolved in a solvent (e.g., physiological saline, buffer or glucose solution), followed by addition of an anti-adsorption agent (e.g., Tween 80, Tween 20, gelatin, or human serum albumin). If desired, the mixture may be freeze-dried so that it is can be redissolved and reconstituted just before use as an injection. Examples of excipients used for freeze-drying include, but are not limited to, sugar alcohols such as mannitol or saccharides such as glucose.

The effective dose of an antibody is appropriately selected depending on the type of the antibody, the type of the disease to be treated or prevented, the age of the patient, the severity of the disease, etc. For example, when the antibody is an anti-glypican antibody to be used as an anticancer agent, the effective dose of the anti-glypican antibody is selected from a range of 0.001 mg to 1000 mg per kg body weight per administration. Alternatively, a dose of 0.01-100,000 mg/body may be selected per patient. However, the effective dose is not limited to these dose levels.

The antibody may be administered either orally or parenterally. Preferably, parenteral administration is used. Specifically, injection (e.g., systemic or local administration by intravenous injection, intramuscular injection, intraperitoneal injection, subcutaneous injection or the like), nasal administration, pulmonary administration, transdermal administration or the like may be enumerated.

Since the method of the present invention for measuring total binding activity is capable of measuring the desired antigen binding activity and antibody-dependent cell-mediated cytotoxicity of a sample antibody simultaneously, this method may be used as a technique for selecting those antibodies which have both high antigen binding activity and excellent antibody-dependent cell-mediated cytotoxicity.

With respect to operations in the method of measuring total binding activity, the following procedures are contemplated by way of example.

1) A donor or an acceptor is directly attached to an antigen peptide or a fragment thereof using a labeling kit or the like (through covalent bond with —$NH_2$ group or —SH group), or indirectly attached thereto by a known method through an antibody such as anti-6XHis antibody; protein anti-human IgG antibody, anti-mouse IgG antibody, anti-rabbit IgG antibody, streptavidin, biotin, ubiquitin, anti-GST antibody, anti-DNP antibody, anti-c-Myc antibody, anti-FLAG antibody, anti-HA antibody or the like, to thereby prepare an antigen solution.

2) Similarly, the donor or the acceptor that was not used in 1) is directly attached to an Fc receptor or a fragment thereof using a labeling kit or the like (through covalent bond with —$NH_2$ group or —SH group), or indirectly attached thereto by a known method through an antibody such as anti-6XHis antibody; protein G, anti-human IgG antibody, anti-mouse IgG antibody, anti-rabbit IgG antibody, streptavidin, biotin, ubiquitin, anti-GST antibody, anti-DNP antibody, anti-c-Myc antibody, anti-FLAG antibody, anti-HA antibody or the like, to thereby prepare an Fc receptor solution.

3) An antibody solution (which is a sample) is diluted gradually with a buffer.

4) The solutions from 1), 2) and 3) are mixed at an appropriate ratio.

5) The solution prepared in 4) is irradiated with light having a wavelength capable of exciting the donor (e.g., light with a wavelength of about 320 nm when the donor is europium chelate) and the fluorescent signals generated are measured by a known method using a plate reader or the like. For example, when the donor is europium chelate and the acceptor is allophycocyanin, fluorescent signals at about 665 nm (fluorescence emitted from the acceptor by FRET) and at about 615 nm (fluorescence emitted by the donor by direct excitation) are measured.

Specifically, measurement may be performed under the following conditions.

[Measuring Conditions]
Excitation: 320 nm; Emission: 665 nm/$2^{nd}$ Emission: 615 nm
Number of flashing times: 200-400, preferably 300
Excitation light is applied through an optical filter of 320 nm (bandwidth: 75 nm). After a delay time of 50-100 μs, preferably 70 μs, the resultant fluorescent signals are measured with optical filters of 665 nm (bandwidth: 7.5 nm) and 615 nm (bandwidth: 8.5 nm) for a window time (measuring time) of 300-500 μs, preferably 400 μS.

The buffer to be used in this measuring method is not particularly limited. As representative examples, phosphate buffer, acetate buffer, Tris-HCl buffer and citrate buffer may be enumerated. The pH at the time of reaction is not particularly limited. The pH may be within a range from 3 to 9.5, preferably 5 to 8.5.

The present invention also provides a kit comprising the following (a) to (c):

(a) a set of donor and acceptor capable of fluorescent resonance energy transfer
(b) an antigen or antigen epitope
(c) an Fc receptor or a fragment thereof.

The donor and the acceptor capable of fluorescent resonance energy transfer are as described earlier and then may be bound to an antibody such as anti-6XHis antibody; protein G, anti-human IgG antibody, anti-mouse IgG antibody, anti-rabbit IgG antibody, streptavidin, biotin, ubiquitin, anti-GST antibody, anti-DNP antibody, anti-c-Myc antibody, anti-FLAG antibody, anti-HA antibody or the like. When they are bound to such an antibody or the like, the kit may include a reagent for adding a His tag to the antigen or the Fc receptor, a regent for binding biotin to the antigen or the Fc receptor, or the like. The antigen or antigen epitope and the Fc receptor or a fragment thereof are as described earlier. This kit may be used for measuring total binding activity, quality control of antibodies, and screening of antibodies.

Further, this kit may include a buffer containing Tris-HCl, EDTA, NaCl, TRITON™ X-100, DTT or the like; a reactor such as a microplate; and an instruction manual.

Still further, the present invention provides a kit comprising the following (a) to (d):

(a) a set of donor and acceptor capable of fluorescent resonance energy transfer
(b) an antigen or antigen epitope
(d) an antibody-binding molecule or a fragment thereof.

The donor and the acceptor capable of fluorescent resonance energy transfer are as described earlier and they may be bound to an antibody such as anti-6XHis antibody; protein G, anti-human IgG antibody, anti-mouse IgG antibody, anti-rabbit IgG antibody, streptavidin, biotin, ubiquitin, anti-GST antibody, anti-DNP antibody, anti-c-Myc antibody, anti-FLAG antibody, anti-HA antibody or the like. When they are bound to such an antibody or the like, the kit may include a reagent for adding a His tag to the antigen or the Fc receptor, a regent for binding biotin to the antigen or the Fc receptor, or the like. The antibody-binding molecule or a fragment thereof is as described earlier. This kit may be used to measure the binding activities of an antibody to both an antigen or antigen epitope and an antibody-binding molecule or a fragment thereof, or to screen for antibodies with a biological activity that results from antibody binding to both an antigen or antigen epitope and an antibody-binding molecule or a fragment thereof.

Further, this kit may include a buffer containing Tris-HCl, EDTA, NaCl, TRITON™ X-100, DTT or the like; a reactor such as a microplate; and an instruction manual.

EXAMPLES

Hereinbelow, the present invention will be described more specifically with reference to Examples. These Examples are provided only for the purpose of illustrating the present invention and are not intended to limit the scope of the present invention.

Example 1

Preparation of Antibody

[Method of Preparing Anti-Glypican-3 Antibody (Anti-GPC3 Antibody)]

Anti-glypican-3 antibody (anti-GPC3 antibody)-expressing CHO cells (Example 4 in WO2006/06693) were expanded by culture. The culture broth was filtered to remove cells (CM fraction). This CM fraction was subjected to an rProteinA Sepharose step. The eluted fraction was neutralized and filtered, and then concentrated with a TFF membrane, followed by exchange of buffer. By these procedures, samples of Lot Nos. ON0305J01 (4.5% aFuc, quantified as 28.5 mg/mL), A5-3 (4.7% aFuc, quantified as 6.88 mg/mL), J1-2 (3.3% aFuc, quantified value 6.54 mg/mL), N2-3 (6.7% aFuc, quantified as 5.54 mg/mL) and Mo0305125 (3.0% aFuc, quantified as 8.18 mg/mL) were prepared.

Aside from the above five samples, a sample of Lot No. Mo03FTP-050725 with a different afucosyl (aFuc) content (96.8% aFuc, quantified as 1 mg/mL) was obtained by the method described in WO2006/46751.

[Afucosyl Anti-GPC3 Antibody Producing Cells]

Afucosyl anti-GPC3 antibody producing cells were prepared by the method described in WO2006/46751, and used in this Example.

[Preparation of Afucosyl Anti-GPC3 Antibody]

Afucosyl anti-GPC3 antibody expressing CHO cells were cultured. From the resultant culture supernatant, afucosyl anti-GPC3 antibody was obtained using protein A affinity column chromatography and ion exchange column chromatography.

Briefly, after addition of the culture supernatant to an rProtein A Sepharose FF column (GE Health Care Bioscience) and washing the column, the protein adsorbed onto the column was eluted with acid. The pH of the eluted fraction was adjusted to a circumneutral value. The afucosyl GC33-containing fraction was added to an SP Sepharose FF column (GE Health Care Bioscience) equilibrated with 20 mM acetate buffer, at pH 6.0. After washing the column with the same buffer, the protein adsorbed onto the column was eluted with the same buffer containing 200 mM NaCl.

The resultant fraction was analyzed by SDS-PAGE. Afucosyl anti-GPC3 antibody-containing fractions were collected to obtain a final preparation.

Samples of the two lots indicated below were diluted to the same concentration (this time, 1 mg/mL) and mixed as follows.

| | aFuc content |
|---|---|
| 100% (actually 96.8%) | 100% Mo03FTP-050725 |
| 50% (50.7%) | mixture of 50% Mo03FTP-050725: 50% ON0305J01→(1) |
| 25% (27.6%) | mixture of 50% (1): 50% ON0305J01 |
| 5% (4.5%) | 100% ON0305J01 |

Example 2

Preparation of Fc Receptor V-Type (FcγRIIIaV-6xHis)

FcγRIIIaV fragment+6xHis tag-expressing CHO cells were prepared as described below. Briefly, a soluble CD16 cDNA encoding human CD16 extracellular domain was amplified by PCR using Multiple Tissue cDNA panels: Fetal spleen cDNA library (Clontech) as a template. The primers used were CD16F1 (TAA GAA TTC CCA CCA TGT GGC AGC TGC TCC TCC C) (SEQ ID NO: 5) to which an EcoRI recognition sequence and a Kozak sequence had been added as 5' terminal synthetic oligos and CD16R1 (TAA GCG GCC GCT TAT CAA TGA TGA TGA TGA TGA TGA CCT TGA GTG ATG GTG ATG TTC) (SEQ ID NO: 6) to which a His tag, a termination codon and an NotI recognition sequence had been added as 3' terminal synthetic oligos. The resultant PCR product was cloned into a pGEM T-Easy vector. The nucleotide sequence of the thus cloned CD16 was examined by sequencing. As a result, it was confirmed that the cloned CD16 was 158F type in which position 158 is phenylalanine. Using the resultant 158F type gene as a template, a point mutation of F(TTT)→V(GTT) was introduced thereinto using Quick Change (QIAGEN) to thereby obtain a 158V type gene. The thus obtained 158V type gene was cleaved with EcoRI and NotI, followed by cloning into pCXND3'. Hereinbelow, the flow of construction of this vector pCXND3 will be described. Briefly, in order to separate the antibody heavy chain gene and the vector of DHFR-Δ E-rvH-PM1-f (see WO 92/19759), the plasmid was digested at EcoRI/SmaI restriction sites to recover the vector moiety alone. Then, EcoRI-NotI-BamHI adaptor (TaKaRa) was cloned thereinto. The resultant vector was designated pCHOI. The DHFR gene expression site of pCHOI was cloned into the HindIII restriction site of pCXN (Niwa et al, Gene 1991; 108:193-200) to thereby obtain a vector designated pCXND3. Each expression plasmid was introduced into CHO cells by electroporation. By selection with geneticin, soluble CD16 constitutively expressing CHO cells (158V type) were obtained.

These cells were cultured in CHO-S-SFMII (Invitrogen) containing 0.5 mg/mL geneticin (Invitrogen) and 1% penicillin-streptomycin (Invitrogen) at 37° C. under 8% $CO_2$.

Soluble CD16V (158V type) was prepared from the resultant culture supernatant using cation exchange ion chromatography and affinity column chromatography for His tag.

Briefly, SP Sepharose FF column (GE Health Care Bioscience) equilibrated with 20 mM acetate buffer (pH 5.0) was added with the culture supernatant diluted 3-fold with the same buffer. After washing the column with the same buffer, the protein adsorbed onto the column was eluted with the same buffer containing 500 mM NaCl. The resultant fractions were analyzed by Western blotting using a His tag specific antibody to thereby collect soluble CD16 (158V type)-containing fractions.

The soluble CD16 (158V type) fractions obtained by cation exchange column chromatography were adjusted to pH 7.0 with 1 M Tris and added to Talon Metal Affinity Resin column (Clontech) equilibrated with 20 mM sodium phosphate buffer containing 300 mM NaCl at pH 8.0. After washing the column with the same buffer, the protein adsorbed onto the column was eluted with a linear concentration gradient of imidazole from 0 mM to 150 mM in the same buffer. The resultant fractions were analyzed by SDS-PAGE to collect soluble CD16 (158V type)-containing fractions.

Each of the fractions obtained by affinity column chromatography for His tag was concentrated through an ultrafiltration membrane (Amicon Ultra-15; molecular weight cutoff value, 10 kDa; Millipore), and the buffer was replaced with PBS. Thus, a final preparation was obtained.

Example 3

Preparation of Fc Receptor F-Type (FcγRIIaF-6xHis)

FcγRIIIaF fragment+6xHis tag-expressing CHO cells were prepared as described below. Briefly, a soluble CD16 cDNA encoding human CD16 extracellular domain was amplified by PCR using Multiple Tissue cDNA panels: Fetal spleen cDNA library (Clontech) as a template. The primers used were CD16F1 (TAA GAA TTC CCA CCA TGT GGC AGC TGC TCC TCC C) (SEQ ID NO: 5) to which an EcoRI recognition sequence and a Kozak sequence had been added as 5' terminal synthetic oligos and CD16R1 (TAA GCG GCC GCT TAT CAA TGA TGA TGA TGA TGA TGA CCT TGA GTG ATG GTG ATG TTC) (SEQ ID NO: 6) to which a His tag, a termination codon and an NotI recognition sequence had been added as 3' terminal synthetic oligos. The resultant PCR product was cloned into a pGEM T-Easy vector. The nucleotide sequence of the thus cloned CD16 was examined by sequencing. As a result, it was confirmed that the cloned CD16 was 158F type in which position 158 is phenylalanine. The thus obtained 158F type gene was cleaved with EcoRI and NotI, followed by cloning into pCXND3. Hereinbelow, the flow of construction of this vector pCXND3 will be described. Briefly, in order to separate the antibody heavy chain gene and the vector of DHFR-Δ E-rvH-PM1-f (see WO 92/19759), the plasmid was digested at EcoRI/SmaI restriction sites to recover the vector moiety alone. Then, EcoRI-NotI-BamHI adaptor (TaKaRa) was cloned thereinto. The resultant vector was designated pCHOI. The DHFR gene expression site of pCHOI was cloned into the HindIII restriction site of pCXN (Niwa et al, Gene 1991; 108:193-200) to thereby obtain a vector designated pCXND3. Each expression plasmid was introduced into CHO cells by electroporation. By selection with geneticin, soluble CD16 constitutively expressing CHO cells (158F type) were obtained.

These cells were cultured in CHO-S-SFMII (Invitrogen) containing 0.5 mg/mL geneticin (Invitrogen) and 1% penicillin-streptomycin (Invitrogen) at 37° C. under 8% $CO_2$.

The resultant culture supernatant was added to Talon Metal Affinity Resin column (Clontech) equilibrated with 20 mM sodium phosphate buffer containing 300 mM NaCl at pH 8.0. After washing the column with the same buffer, the protein adsorbed onto the column was eluted with a linear concentration gradient of imidazole from 0 mM to 500 mM in the same buffer. The resultant fractions were analyzed by SDS-PAGE to collect soluble CD16 (158F type)-containing fractions.

The purified fractions were subjected to dialysis to replace the buffer with PBS. Thus, a final preparation was obtained.

Example 4

Method of Testing the Antigen Binding Activity and FcR Binding Activity (Total Binding Activity) of Anti-Glypican-3 Antibody (Anti-GPC3 Antibody) by TR-FRET 1.1 Reagents and Sample Solutions
Eu-W1024 labeled anti-6xHis antibody (Eu-anti 6xHis) (Perkin Elmer)
Streptavidin conjugated to SureLight™-allophycocyanin for kinase assays (StAv-APC) (Perkin Elmer)
Biotinylated GPC3 epitope peptide (B-GPC3epi: amino acid sequence
Biotin-SQQATPKDNEISTFNHLGNV (SEQ ID NO: 1)) (SIGMA GENOSYS)
Fc receptor V-type (FcγRIIIaV-6xHis) (prepared in Example 2)
Fc receptor F-type (FcγRIIIaF-6xHis) (prepared in Example 3)
2-Amino-2-hydroxylmethyl 1,3-propanediol (Tris) (special grade chemical) (Wako Pure Chemical Industries)
EDTA•2Na (Wako Pure Chemical Industries)
Sodium chloride (special grade chemical) (Wako Pure Chemical Industries) TRITON™ X-100, (Promega).
Dithiothreitol (DTT) (special grade chemical) (Wako Pure Chemical Industries)
5 mol/L hydrochloric acid (for volume analysis) (Wako Pure Chemical Industries)

Figure 3:
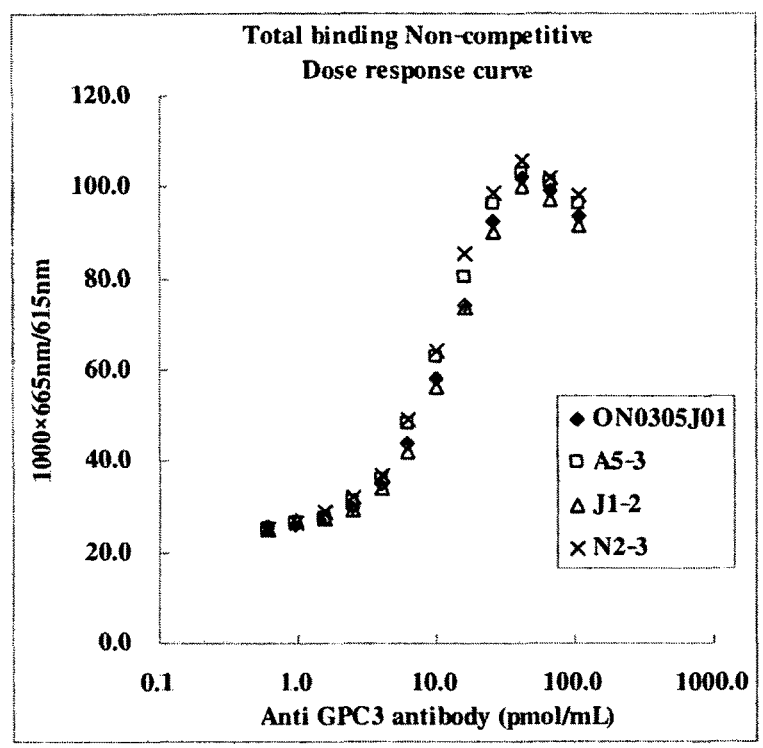
FIG. 3 shows the total binding non-competitive dose response curve of anti-glypican-3 antibody (anti-GPC3 antibody) drug substance.
Figure 4:
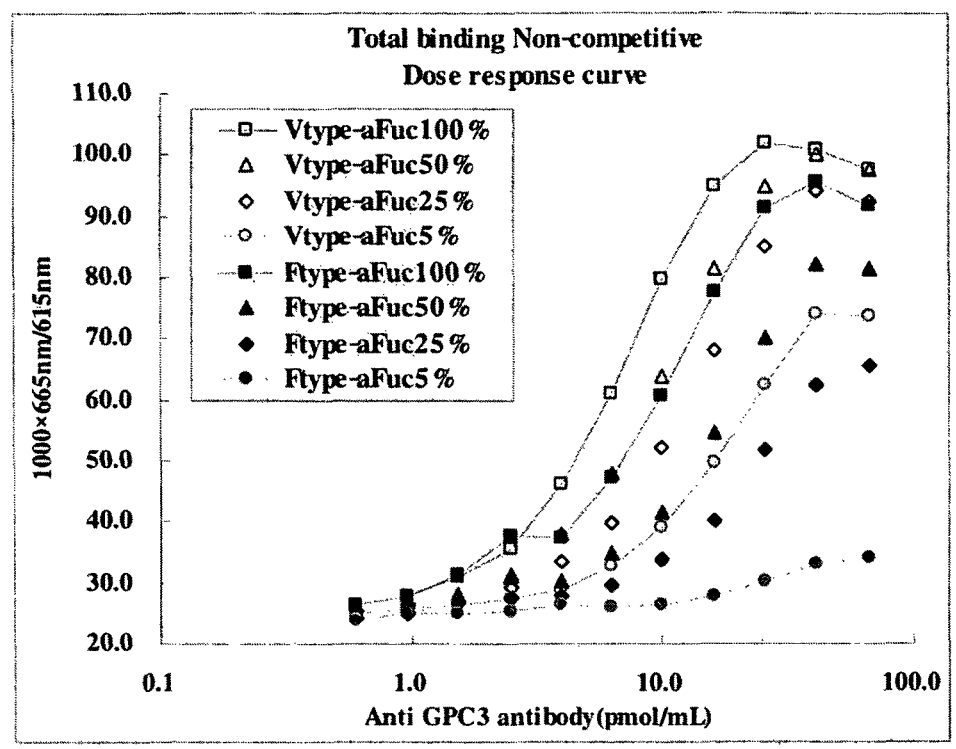
FIG. 4 shows the total binding non-competitive dose response curves of samples with varied aFuc contents.

1.2 Instruments and Apparatus
Preparation plate: Optical 96-well Reaction plate (Applied Biosystems)
384 White Microplate: OptiPlate 384 (Perkin Elmer)
Microplate reader: EnVision 2102 (Perkin Elmer)
Control software: Wallac EnVision Manager ver.1.07 (Perkin Elmer)
Balance: PG503-SDR (METTLER TOLEDO)
pH meter: HM-50G (DKK-TOA Corporation)
Ultrapure water preparation apparatus: Autopure ER 600G (Yamato Science)
1.3 Test Method
StAv-APC solution[*1] was diluted with a binding buffer[*2] to give a concentration of 400 pmol/mL (APC concentration) [Solution A].
B-GPC3epi solution[*3] was diluted with a binding buffer[*2] to give a concentration of 800 pmol/mL [Solution B].
FcγRIIIaV-6xHis was diluted with a binding buffer[*2] to give a concentration of 400 pmol/mL [Solution C].
Eu-anti 6xHis was diluted with a binding buffer[*2] to give a concentration of 5 pmol/mL [Solution D].
Solution A and Solution B were mixed at 1:1 [Mixture-1] and left to stand in the dark at room temperature for 30 min.
Solution C and Solution D were mixed at 1:1 [Mixture-2] and left to stand in the dark at room temperature for 30 min.
The drug substance of anti-glypican-3 antibody (anti-GPC3 antibody) prepared in Example 1 was diluted gradually with a binding buffer[*2] [Solution E].
Mixture-1 (20 μL), Mixture-2 (20 μL) and gradually diluted Solution E (10 μL) were mixed in a preparation plate, and the resultant mixture was transferred in 40-μL aliquots to the 384 white microplate for measurement with a plate reader.
[Measuring Conditions]
Excitation: 320 nm; Emission: 665 nm/2.sup.nd Emission: 615 nm Excitation light was applied through an optical filter of 320 nm (bandwidth: 75 nm) with 300 flashing times. After a delay time of 70 .mu.s, the resultant fluorescent signals were measured with optical filters of 665 nm (bandwidth: 7.5 nm) and 615 nm (bandwidth: 8.5 nm) for a window time (measuring time) of 400 .mu.s. *1 StAv-APC solution: Distilled water (1 mL) was added to 1 vial of streptavidin conjugated to SureLight™-allophycocyanin for kinase assays (Perkin Elmer) and the solution was left to stand on ice for 20-30 min. The resultant solution was agitated by vortexing or pipetting just before use. *2 Binding buffer: 50 mmol/L Tris-HCl pH 7.4, 1 mmol/L EDTA, 150 mmol/L NaCl, 0.1% TRITON™ X-100, 1 mmol/L DTT *3 PBS (phosphate-buffered saline; Invitrogen) was added to 1 vial of biotinylated GPC3 epitope peptide (synthetic peptide manufactured by SIGMA GENOSYS) to give a concentration of 1 mg/mL.
2. Test Results
FIG. 3 shows dose response curves of total binding activity caused by non-competitive reaction of the anti-glypican-3 antibody stock solution (Total Binding Non-Competitive Dose Response Curve), using Fc receptor V-type with aFuc contents of 4.5% in ON0305J01, 4.7% in A5-3, 3.3% in J1-2, and 6.7% in N2-3. ON0305J01, A5-3, J1-2 and N2-3 represent the lots designations of the anti-glypican-3 antibody (anti GPC3 antibody) drug substance. In the total binding activity test, good dose response curves were obtained that should enable a difference between lots to be confirmed on samples with slightly different afucosyl contents. Further, linear model analysis (pallarel line method) performed in the linear range made it possible to calculate specific binding activities. Thus, quantitative evaluation should be possible.
FIG. 4 shows dose response curves of total binding activity caused by non-competitive reaction of anti-glypican-3 antibodies (anti GPC3 antibodies) with different afucosyl (aFuc)

contents (these antibodies bind to each of FcγRIIaV-6xHis and FcγRIIIaF-6xHis) (Total Binding Non-Competitive Dose Response Curve). When a non-competitive system was measured on the samples with different aFuc contents, dose response curves correlating with the aFuc content could be confirmed. Suggesting correlation between the aFuc content and the binding activity, similarly, ADCC test also shows dose response curves correlating with the aFuc content (data not shown). Therefore, it was believed that TR-FRET is linked to ADCC test. Unlike those shown in FIG. 3, the test samples in FIG. 4 are believed to have an identical affinity for antigen binding; and the difference between test samples in Fc receptor binding as part of the total binding activity could be confirmed. Further, it is said that an Fc receptor of F-type is generally weaker affinity than V-type. It is believed that the degree of difference in affinity between V-type and F-type can be seen from the dose response curves.

Figure 5:
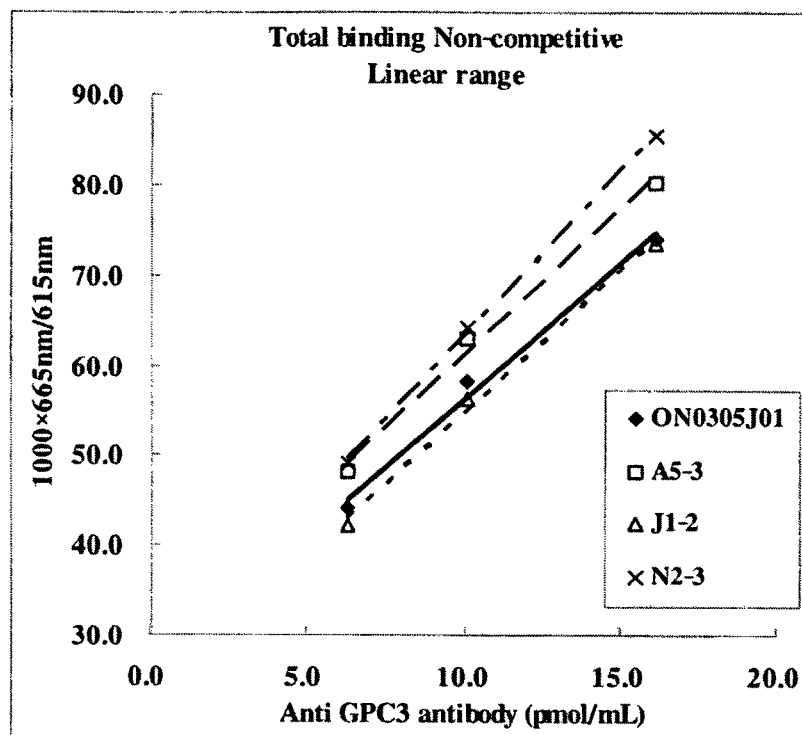
FIG. 5 is a graph showing the results of measuring the total binding non-competitive responses of ON0305J01, A5-3, J1-2 and N2-3 in the provisional linear range.

From the provisional linear range of ON0305J01, A5-3, J1-2 and N2-3 (FIG. 5), specific activities were calculated by the 3+3 parallel line method. Calculation procedures were according to the calculation method described in European Pharmacopoeia 5.3 Statistical Analysis. Using the linear range of dose response curves, binding activity ratios were calculated by parallel line model analysis. Mo03050125 is an anti-glypican-3 antibody (anti-GPC3 antibody) prepared before ON0305J01. The time of preparation is in the following order from the earliest to the newest: Mo03050125, A5-3 etc., ON0305J01. Mo03050125 was used in lot analysis in ADCC. Since the amount of Mo03050125 prepared was small, ON0305J01 was used in TR-FRET. The results are shown in Table 1.

TABLE 1

| Lot | aFuc content (%) | Relative binding activity TR-FRET | Potency ADCC | 95% confidence limit TR-FRET | ADCC |
|---|---|---|---|---|---|
| Mo03050125 | 3.0 | — | 1 | — | — |
| ON0305J01 | 4.5 | 1 | — | — | — |
| A5-3 | 4.7 | 1.21 | 0.75 | 1.11-1.31 | 0.48-1.15 |
| J1-2 | 3.3 | 0.95 | 0.91 | 0.90-1.01 | 0.64-1.27 |
| N2-3 | 6.7 | 1.18 | 0.89 | 1.10-1.27 | 0.57-1.38 |

Although no difference between lots is observed in the ADCC test, differences between lots are recognized in TR-FRET. If TR-FRET is linked to ADCC (as hypothesis), it is presumed that differences can be confirmed in the binding activity test (TR-FRET) although no difference can be confirmed in the biological activity test (ADCC).

The method of the present invention for testing antibody binding activity have the following advantages.

Testing operations are simple (after reagent preparation, only mixing and incubation are required). It is a highly robust testing method.

Since 384 plate can be used, a large number of samples can be measured at a time. This test method is easily developed into a high-throughput assay.

The method of the present invention for testing antibody binding activity is not only applicable to quality assessment of antibodies but also applicable in screening methods for antibodies with ADCC activity because it is applicable in high-throughput screening methods.

All publications, patents and patent applications cited herein are incorporated herein by reference in their entirety.

INDUSTRIAL APPLICABILITY

The present invention is applicable to quality assessment of antibodies and screening methods for antibodies with ADCC activity.

SEQUENCE LISTING FREE TEXT

<SEQ ID NO: 1>
SEQ ID NO: 1 shows the amino acid sequence of GPC3 epitope (derived from human).
<SEQ ID NO: 2>
SEQ ID NO: 2 shows the amino acid sequence of FcγRIIIaV (derived from human).
<SEQ ID NO: 3>
SEQ ID NO: 3 shows the amino acid sequence of FcγRIIIaF (derived from human).
<SEQ ID NO: 4>
SEQ ID NO: 4 shows the amino acid sequence of the epitope region of VEGF epitope (derived from human).
<SEQ ID NO: 5>
SEQ ID NO: 5 shows the nucleotide sequence of primer CD16F1.
<SEQ ID NO: 6>
SEQ ID NO: 6 shows the nucleotide sequence of primer CD16R1.

The invention claimed is:

1. A method of detecting the binding of an antibody to both an antigen or antigen epitope and an Fc receptor or a binding fragment thereof simultaneously, comprising:
    mixing the antibody with the antigen or antigen epitope labeled with one member of a set of donor and acceptor capable of fluorescent resonance energy transfer and the Fc receptor or binding fragment thereof labeled with the other member of the set of donor and acceptor;
    irradiating the resultant mixture with light having a wavelength capable of exciting the donor;
    measuring the fluorescence level of said mixture; and
    indicating the binding of the antibody to both the antigen or antigen epitope and the Fc receptor or binding fragment thereof simultaneously based on said fluorescence level, wherein the Fc receptor is selected from the group consisting of FcγR, FcεR, and FcαR.

2. The method of claim 1, wherein the Fc receptor is selected from the group consisting of FcγRI, FcγRII, and FcγRIII.

3. The method of claim 1, wherein the Fc receptor is FcγRIII.

* * * * *